United States Patent [19]

Henkens et al.

[11] Patent Number: 5,368,707
[45] Date of Patent: Nov. 29, 1994

[54] CONVENIENT DETERMINATION OF TRACE LEAD IN WHOLE BLOOD AND OTHER FLUIDS

[75] Inventors: Robert W. Henkens, Durham; Junguo Zhao, Chapel Hill; Marek Wojciechowski, Cary; John P. O'Daly, Carrboro; Zhi-Wei Liang, Durham; Susan E. Morris, Chapel Hill, all of N.C.

[73] Assignee: Andcare, Inc., Durham, N.C.

[21] Appl. No.: 73,806

[22] Filed: Jun. 7, 1993

Related U.S. Application Data

[63] Continuation-in-part of Ser. No. 821,732, Jan. 15, 1992, Pat. No. 5,217,594.

[51] Int. Cl.$^5$ .................. G01N 27/26; G01N 33/20
[52] U.S. Cl. ........................... 204/153.12; 204/153.1; 204/403; 436/74; 436/77
[58] Field of Search ........... 204/153.12, 153.1, 153.17, 204/403, 412, 415, 418; 436/74, 77

[56] References Cited

U.S. PATENT DOCUMENTS

| | | | |
|---|---|---|---|
| 4,090,926 | 5/1978 | Matson | 204/1 T |
| 4,374,041 | 2/1983 | Matson | 436/60 |
| 4,581,336 | 4/1986 | Malloy et al. | 435/176 |
| 4,820,399 | 4/1989 | Senda et al. | 204/403 |
| 4,950,378 | 8/1990 | Nagata | 204/402 |
| 4,970,145 | 11/1990 | Bennetto et al. | 435/14 |
| 5,160,418 | 11/1992 | Mullen | 204/153.12 |
| 5,227,307 | 7/1993 | Bar-Or et al. | 436/74 |
| 5,302,531 | 4/1994 | Bauer | 436/74 |

FOREIGN PATENT DOCUMENTS

WO87/07295 12/1987 WIPO.
WO91/17259 11/1991 WIPO.

OTHER PUBLICATIONS

Albery et al., "Inhibited Enzyme Electrodes. Part 3.," *Biosensors & Bioelectronics,* 5:397-413, 1990, published in Great Britain.

Almestrand et al., "Determination of Lead in Whole Blood with a Simple Flow-Injection System and Computerized Stripping Potentiometry," *Analytica Chimica Acta,* 209:339-343, 1988, published in The Netherlands.

Baum & Czok, "Enzymatische Bestimmung von, ionisiertem Magnesium im Plasma," *Biochemische Zeitschrift,* 332:121-130, 1959.

Botré et al., "Synthesis and Inhibitory Activity on Carbonic Anhydrase of Some New Sulpiride Analogues Studied by Means of a New Method," *Journal of Medicinal Chemistry,* 29:1814-1020, 1986.

"New Rules Set for Blood Lead Levels," *Chemical and Engineering News,* p. 17, Oct. 14, 1991.

Fair & Jamieson, "Studies of Protein Adsorption On Polystyrene Latex Surfaces," *Journal of Colloid and Interface Science,* 77(2):525-534, 1980.

Guilbault et al., "Homovanillic Acid as a Fluorometric Substrate for Oxidative Enzymes," *Analytical Chemistry,* 40(1):190-196, 1968.

Guilbault, "Determination of Inhibitors," *Enzymatic Methods of Analysis,* Pergamon Press, pp. 197-209, 1970, published in Great Britain.

Holleck, "The Reduction of Chlorine on Carbon in AlCl$_3$-KCl, NaCl Melts," *Journal of the Electrochemical Society,* 119(9):1158-1161.

"U.S. CDC Releases Revised Guidelines on Childhood Lead Poisoning-Blood Lead Level of Concern Lowered to $\geq$10 µg/dl," *ILZRO Environmental Update,* 1(10):2, 1991.

(List continued on next page.)

*Primary Examiner*—John Niebling
*Assistant Examiner*—Bruce F. Bell
*Attorney, Agent, or Firm*—Arnold, White & Durkee

[57] ABSTRACT

The invention relates to methods of determining micromolar levels of lead ion in various fluids, including blood. Detection of lead or other heavy metal ion concentrations as low as 1 µg/dL is achieved. The methods are adaptable to the detection of low levels of lead in whole blood, employing a novel separation and release of lead ion from lead chelating agents. The disclosed methods employ isocitrate dehydrogenase-based electrodes which are particularly suited for detecting nanomolar levels of lead.

11 Claims, 6 Drawing Sheets

OTHER PUBLICATIONS

Kamata & Onoyama, "Lead-Selective Membrane Electrode Using Methylene Bis(diisobutyldithiocarbamate) Neutral Carrier," *Analytical Chemistry*, 63:1295–1298, 1991.

Kratochvil et al., "Effect of Metals on the Activation and Inhibition of Isocitric Dehydrogenase," *Analytical Chemistry*, 39(1):45–51, 1967.

Linde, "Estimation of Small Amounts of Fluoride in Body Fluids," *Analytical Chemistry*, 31(12):2092–2094, 1959.

Morrissey & Han, "The Conformation of γ-Globulin Adsorbed on Polystyrene Latices Determined by Quasielastic Light Scattering," *Journal of Colloid and Interface Science*, 65(3):423–431, 1978.

Sheikh & Townshend, "Applications of Enzyme-Catalysed Reactions in Trace Analysis-VII," *Talanta*, 21:401–409, 1974 published in Great Britain.

Smit & Cass, "Cyanide Detection Using a Substrate-Regenerating, Peroxidase-Based Biosensor," *Analytical Chemistry*, 62:2429–2436, 1990.

Toren & Burger, "Trace Determination of Metal Ion Inhibitors of the Glucose-Glucose Oxidase System," *Mikrochimica Acta (Wien)*, pp. 538–545, 1968.

Tran-Minh et al., "Studies on Acetylcholine Sensor and its Analytical Application Based on the Inhibition of Cholinesterase," *Biosensors & Bioelectronics*, 5:461–471, 1990.

Smith, "Air Pollution and Forest Damage," *Chemical and Engineering News*, pp. 30–42, Nov. 11, 1991.

Trade Brochure: esa, Inc. Trace Metal Analyzer Brochure, Bedford, Mass., 1990.

Gunasingham et al., "Performance and Evaluation of a Handheld Electrochemical Monitor for Toxic Metals," Cole-Parmer Instrument Company, Chicago, Ill.

Crumbliss, A. L., Henkens, R. W., Kitchell, B. S., Perine, S. C., Stonehuerner, J., and Tubergen, K. R., "Amperometric Glucose Sensor Fabricated from Glucose Oxidase and a Mediator Co-Immobilized on a Colloidal Gold Hydrogel Electrode," *Biosensors Technology: Fundamentals and Application*, Chapter 13, 1990, published in USA.

Crumbliss, A. L., Henkens, R. W., Hunter, K., Kitchell, B. S. O'Daly, J. P., Stonehuerner, J., and Tubergen, K. R., "The Influence of Colloidal Gold Surfaces on Enzyme Activity," ACS North Carolina Divisional Meeting, Sep. 1988, published in USA.

Crumbliss, A. L., Henkens, R. W., Kitchell, B. S., Perine, S. C., Stonehuerner, J., and Tubergen, K. R., "Amperometric Glucose Sensor Fabricated from Glucose Oxidase and a Mediator Co-Immobilized on a Colloidal Gold Hydrogel Electrode," ACS North Carolina Divisional Meeting, University of North Carolina at Chapel Hill, Sep. 7–9, 1989, published in USA.

Crumbliss, A. L., Kitchell, B. S., Perine, S. C., Stonehuerner, J., Tubergen, K. R., Zhao, J., and Henkens, R. W., "Catalytic and Electroactivity of Irreversibly Adsorbed Enzymes at Gold Electrode Surfaces," Symposium on Protein Electrochemistry: ACS Southeast Regional Meeting (SERM), Oct. 1989, published in USA.

Crumbliss, A. L., Henkens, R. W., Kitchell, B. S., McLachlan, K. L., O'Daly, J. P., Perine, S. C., Stonehuerner, J., Tubergen, K. R., and Zhao, J., "The Use of Inorganic Materials to Control or Maintain Immobilized Enzyme Activity," Symposium on opportunities for inorganic chemistry in biotechnology, ACS National Meeting in Boston, Apr. 23, 1990, published in USA.

Henkens, R. W., Kitchell, B. S., O'Daly, J. P., Perine, S. C., and Crumbliss, A. L., "Bioactive Electrodes Using Metallo Proteins Attached to Colloidal Gold," *Recl.: Trav. Chim. Pays Bas*, 106:298, 1987.

Henkens, R. W., Zhao, J., and O'Daly, J. P., "Multi-Analyte Enzyme Electrodes for Environmental Monitoring," *Proceedings of 5th International Biotechnology Conference in Copenhagen*, Jul. 8–13, 1990.

Sakai et al., "Determination of Heavy Metal Ions by Urea Sensor Using ISFET," *Sensors and Materials*, 2(4):217–227, 1991.

Sheikh, R. A., "The Determination of Nanogram Amounts of Indium, Lead and Drugs of Forensic Importance by Enzymic Inhibition," *Proc. Soc. Analyt. Chem.*, 10(11):263–286, 1973.

PCT Search Report maield Apr. 5, 1993.

CONVENIENT DETERMINATION OF TRACE LEAD IN WHOLE BLOOD AND OTHER FLUIDS

This is a continuation-in-part of co-pending application Ser. No. 07/821,732 filed Jan. 15, 1992, U.S. Pat. No. 5,217,594, issued Jun. 8, 1993.

The entire text of U.S. Pat. No. 5,217,594 is incorporated herein by reference without disclaimer.

BACKGROUND OF THE INVENTION

1. Field of the Invention

The invention relates to novel methods employing immobilized enzyme biosensors to determine micromolar levels of lead. Also disclosed are methods of releasing lead from complexes to make the lead available for detection, by conventional assay or by various electrochemical methods based on enzyme catalyzed reactions. The disclosed methods are adaptable to the rapid, efficient detection of lead ion in whole blood, employing a unique metal replacement of lead ion from a capture complex.

2. Description of Related Art

Heavy metals such as lead have received increasing recognition as serious threats to the environment and to human health. The effects of lead may not be acute; indeed chronic toxicity is of particular concern because this metal accumulates in tissues over a period of long-term exposure. This may lead to mental and physical abnormalities, especially in the very young.

The detrimental effects of lead in the environment have long been recognized. Lead poisoning has been detected in waterfowl due to lead shot. The elimination of tetraethyl lead as an octane booster in gasoline was part of an effort to prevent this metal from further contamination of soil and water supplies. However, the use of lead in glazes, paints and coatings, to mention a few examples, has occurred over long periods of time; in fact, lead in pottery may have contributed to the demise of earlier civilizations.

As a result of past long-term use of lead in a wide range of products, it is difficult to avoid exposure to this element. Lead solder joints in water pipes, for example, contribute to the lead content of drinking water. Modern interior paints are lead-free, but in older homes there may be significant exposure to lead in the surroundings from older lead-based paints, even when such paint layers are coated with the newer lead-free paints. Unfortunately, this has created a real risk of lead toxicity for those groups most susceptible, especially children.

The long term effect of lead on the health of children exposed to unacceptable levels is calculated to be very significant. This will ultimately reflect in higher health costs, due to increased disability and treatment required. This is of concern to health care professionals and to the federal government, to the extent that new rules related to a "threshold of concern" have been provided in guidelines set by Health & Human Services' Centers for Disease Control (C&E News, 1991). It is hoped that programs being developed to detect the presence of lead in groups at risk for the most damage from lead poisoning will lead to rapid, reliable methods of detecting low levels of lead in individuals. Unfortunately, it is difficult at best to detect lead in body fluids such as blood and it would be impractical to take tissue samples, for example brain tissue samples, to determine lead concentrations.

A simple, reliable method of detecting levels of lead in blood is not available. Current technology relies on time-consuming methods such as computerized stripping potentiometry (Almestrand, et al., 1988). Although the instrumentation required for this determination is not unduly complex, skilled technicians are needed.

Instruments currently available for monitoring trace metals generally require highly trained personnel to perform relatively sophisticated techniques. Consequently, analyses are performed in centralized laboratories set up for routine multiple sample analysis. However, there is no instrumentation available for use in the field or in the physician's office allowing rapid metal determinations with simple portable instruments that do not require highly technically trained personnel.

Trace heavy metal determination based on metal-enzyme interaction has taken advantage of either activation or inhibition of an enzyme by a metal, usually specific for the enzyme. Fluoride has been measured by its inhibition of liver esterase catalysis of a butyrate substrate (Linde, 1959) and magnesium has been measured in plasma by isocitric dehydrogenase activation (Baum and Czok, 1959). Titration determinations or rates of TPNH formation measured spectrophotometrically have been reported to be useful for measuring levels of activating metals such as manganese, magnesium and cobalt. Inhibiting metals such as lead can also be measured (Kratochvil, et al., 1967).

Analysis of lead based on inhibition of an enzyme's ability to produce hydrogen peroxide and oxidize homovanillic acid to a fluorescent product has also been explored. Horseradish peroxidase inhibition was linear over a range of 10–185 $\mu g/ml$ of lead (Guilbault, et al., 1968). Metal ion inhibition of the enzyme glucose oxidase with mercury(II), Ag(I) and Pb(II) has suggested that these metals are detectable at low levels although strong buffer-interactions were obtained when lead was present, casting doubt on the viability of the method generally to measure lead in trace amounts (Toren and Burger, 1968).

Of a few reported enzyme-inhibitor electrodes employed to measure trace heavy metals, most use $CO_2$ and pH electrodes (Tran-Minh et al., 1990; Botre et al., 1983) which have a small, nonlinear response. Potentiometric sensors typically are used to detect the enzymatic reaction product, not the enzyme activity directly. The response time to inhibitors tends to be long because the inhibition manifests only after the product has diffused away from the electrode surface. When a pH electrode is used, the signal largely depends on the pH and the buffer capacity of the sample solution.

While an enzyme inhibitor sensor is desirable for selective measurement of lead ion, additional problems are encountered, particularly in whole blood samples where blood components, particularly blood proteins, tend to interfere with lead/enzyme interactions. Methods to determine lead levels directly in whole blood samples in the presence of interferants are desirable, and particularly one would seek to employ enzyme sensors which are particularly sensitive to inhibition by lead ion. The challenge therefore is to develop a rapid, selective method of detecting lead in blood without excessive manipulation, complex equipment or the need for highly skilled personnel.

SUMMARY OF THE INVENTION

The present invention addresses one or more of the foregoing problems in providing simple, reliable methods of detecting lead in blood and other fluids. The methods take advantage of the irreversible inhibition of isocitrate dehydrogenase or other enzymes selectively inhibited by lead ions to determine micromolar levels of lead in various fluids, including blood. In one aspect of the invention, the method employs novel bioelectrodes constructed from adsorbed enzymes. Several versions of biosensors may be employed, including biosensors constructed from novel colloidal gold based bioelectrodes to measure changes in current generated in the presence of an oxidizable substrate and an enzyme cofactor.

The methods of the present invention concern detection of very low levels of heavy metal ions, particularly lead ions, employing isocitrate dehydrogenase based biosensors. The biosensors typically include a reference electrode, a counter electrode and a working electrode, or optionally, a counter electrode combined with the reference electrode. The appropriate enzyme is located on or near the surface of the working electrode. In the presence of a suitable substrate the enzyme catalyzes a redox reaction. Current generated by the redox reaction is adversely affected by metal ions that inhibit the enzyme. In particular, lead ion concentrations in the 1 $\mu g/dL$ range are detectable when the disclosed methods are employed.

The disclosed methods, particularly those employing the disclosed biosensors, may be used to detect lead as well as a wide variety of nontoxic and toxic metal ions including mercury, cadmium, silver, zinc, copper, calcium, manganese, thallium, etc. However, sensitivity and selectivity of the biosensor will depend on the enzyme selected. In order to be effectively inhibited by low metal ion concentrations, it is preferable that the enzyme, or enzymes, selected is strongly and irreversibly inhibited by the metal ion. In most situations, one will desire inhibition in the micromolar or lower ranges of metal ion concentration. Mercury ion, for example, is detected in the nanomolar range employing colloidal gold adsorbed alcohol dehydrogenase biosensors. Lead ion may be quantitatively determined employing immobilized isocitrate dehydrogenase.

A conditional stability or formation constant is an equilibrium constant characterizing the ability of a ligand to bind to a metal ion under particular solution conditions. Unlike the thermodynamic constants, which should be only temperature and ionic strength dependent, the conditional constants include (a) the effect of solution pH on the availability of free ligand for binding (protonation of the ligand), (b) the effect of solution pH on the availability of free metal ion for binding (formation of hydroxide complexes of the metal), and (c) the effect of other competing ligands present in the solution. According to convention, the symbol $K'_{PbX}$ represents the conditional stability constant for PbX complex (where X is a component that binds with $Pb^{+2}$) with inclusion of effect (a) only, while symbol $K''_{PbX}$ denotes the conditional stability constant for PbX complex with inclusion of effects (a) and (b). The concept of conditional stability constant is well known to those of skill in the art and is found in conventional analytical chemistry textbooks.

It will be recognized that enzyme inhibition constants of enzymes selected for special use biosensors may differ depending the physical state of the enzyme. Constants may be quite different for immobilized species compared with the same species in solution. While solution inhibition constants in the nanomolar range may suggest suitability of an enzyme as a detection agent for low levels of inhibition, the constant may change after immobilization, thus requiring some degree of experimentation after potentially suitably enzymes have been selected on the basis of solution inhibition constants. The inventors have found, however, that solution inhibition of isocitrate dehydrogenase by lead is comparable to inhibition by the immobilized enzyme. The disclosed methods of determining low lead concentrations thus provide the option of employing amperometric determination of current inhibition for reactions catalyzed by isocitrate dehydrogenase in solution or by immobilized forms such as the particular colloidal gold biosensors developed by the inventors.

Enzymes useful in the practice of the present invention include a wide variety of redox enzymes. Cofactors typically associated with such enzymes include NADP and NAD. During the oxidation process, NADP or NAD is reduced to NADPH or NADH respectively. While it is not necessary to employ mediators with the methods of the present invention as oxidation currents are detectable without added mediators, mediators may be optionally employed and may under some conditions enhance efficiency. Suitable mediators include ferrocene and its derivatives, ferricyanide, N-methylphenazine methosulfate and related compounds such as N-ethyl phenazinium, phenoxazine and the like. Generally, mediators will be selected based on the electrochemical properties of the bioelectrode which depend on the enzyme and substrates chosen. Mediators are typically utilized in their oxidized forms initially to reduce background signal.

The inventors also contemplate alternate embodiments which employ a working electrode surface-coated with a membranous or gelatinous film. The redox enzyme may be dispersed within the gelatin or membrane material and then applied to the surface of the working electrode. Alternatively, the enzyme applied to the electrode may be covered with a membranous film. Enzyme cofactors such as NADP or NAD may also be included in the gelatinous film with the enzyme. Alternatively, such cofactors may be present in the bulk solution where they may freely enter and exit the membrane material with access to the electrode surface and to the gelatinous film immobilized enzyme. Suitable film materials include substances that are compatible with the enzyme selected. These include any of a variety of carrageenans, such as k-carrageenan, hydrophilic polymers or hydrophilic gels such as agar.

The working electrode surface of the biosensor of the present invention is typically a conducting material such as gold, platinum, or carbon. A preferred surface is carbon.

Biosensors useful in practicing methods of the present invention may optionally include both a cofactor such as NADP or NAD and a mediator. Mediators may be associated with the enzyme through hydrophobic association, ionic interactions or by covalent bonding. Alternatively, mediators or cofactors may also be included within a film used to immobilize selected enzymes near the working electrode surface. It is also possible to coat a mediator on the electrode surface, e.g., an insoluble compound on a surface that will slowly dissolve to provide a relatively low but constant amount of mediator or cofactor.

The invention provides novel methods of detecting lead ion in fluids, particularly with regard to the measurement of lead ion in whole blood samples. A sample suspected of containing lead ion is contacted with the working electrode surface of a bioelectrode. An enzyme substrate, preferably isocitrate, is then added to the sample. Alternatively, it is also possible to coat the substrate on the electrode surface. The presence of lead ion causes the current to decrease compared with current generated in the absence of lead ion. The current decrease is inversely related to lead ion concentrations, and may be used to quantitate lead levels well below 10 $\mu g/dL$. By adjusting enzyme concentration, pH, temperature, etc., the inventors have shown that enzyme sensitivity may be adjusted to particular ranges. For example, at pH 9.0, isocitrate dehydrogenase activity is completely inhibited between 0 and 5.5 $\mu g/dL$ lead ion concentration in a linear fashion, while at pH 8.5 the enzyme is inhibited less than 50% at a lead ion concentration of 16.6 $\mu g/dL$.

The disclosed methods are suitable for determining trace metal ion concentrations in water, waste water, biological fluids such as urine, saliva, sweat, tissue exudate and the like. The method is also adaptable for detecting trace lead ion concentrations in whole blood.

As discussed, a major problem in enzymatically determining blood lead levels is interference by blood components. The inventors have addressed this problem by devising methods of releasing lead from the $Pb^{+2}EDTA$ complexes that are formed when blood samples are drawn into EDTA, as is the case in most clinical situations. In principle, the method depends on a displacement of lead ion from the EDTA complex by another ion, preferably cobalt ion. The released lead ion may then be "captured" by another ligand to which it preferentially binds. The capture agent is selected so as not to interfere with the inhibitory effect on isocitrate dehydrogenase; for example, DMSA, o-phenanthroline and biphenyl will bind tightly to $Pb^{2+}$ but do not interfere with electrochemical detection of lead by ICDH inhibition. The reaction may be further secured by oxidizing the displacing metal in the EDTA complex, i.e., oxidation of Co(II) to Co(III). This results in an irreversible complex of the cobalt with EDTA which should increase the efficiency of the reaction. The inventors have discovered that lead ion not only inhibits ICDH but also binds irreversibly to the enzyme. Irreversible binding indicates that one may select a fairly wide range of binding agents as capture agents for lead ion which would release $Pb^{+2}$ to affect the enzyme.

The disclosed methods are adaptable for measurement of very low levels of lead in aqueous media and in blood. The methods take advantage of the irreversible inhibition of isocitrate dehydrogenase at low lead concentrations but have been especially modified to overcome the interferences encountered in whole blood samples.

DETAILED DESCRIPTION OF THE PREFERRED EMBODIMENTS

Figure 1:
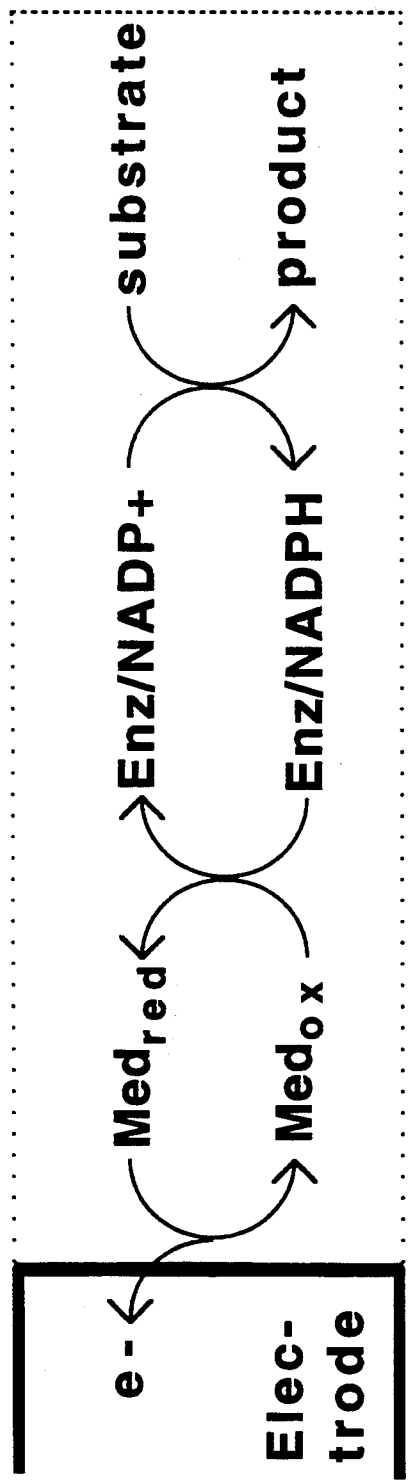
FIG. 1 is a diagram showing the general operating principle of a bioelectrode.

The present invention concerns approaches to and methods for determining lead ion levels in whole blood. Several enzymes are known to be specifically inhibited by heavy metal ions. Isocitrate dehydrogenase for example is inhibited by lead. However, whole blood samples containing lead do not detectably inhibit isocitrate dehydrogenase activity as determined amperometrically. This is likely due to binding of lead by blood proteins such as albumin or other proteins, although it is also possible that the enzyme is stabilized by an unidentified blood component.

Anticoagulants are typically added to blood samples. Although there are numerous compounds with anticoagulant effect, including citrate, the most commonly used are heparin and EDTA. EDTA is generally the anticoagulant of choice in collection of blood samples for clinical analysis. Any lead ion in such treated blood samples will be complexed by EDTA. The challenge therefore was to develop a method to release lead from EDTA and convert it to a form readily detected by an enzyme sensor without inactivating the enzyme or significantly reducing its selectivity and sensitivity.

The inventors have explored two methods to generate release of lead ion from the $Pb^{2+}EDTA$ complex. The first method is a displacement of lead by cobalt(II). $Co^{2+}EDTA$ is less stable than $Pb^{2+}EDTA$. The conditional stability constant for $Co^{2+}EDTA$ at pH 8.5 is $10^{14.65}$. The stability constant for $Pb^{2+}EDTA$ is $10^{15.11}$. The following reaction:

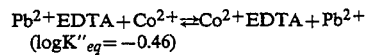

is not thermodynamically favorable at pH 8.5. Even large excesses of $Co^{2+}$ will not result in quantitative displacement of $Pb^{2+}$. However, complex distribution calculations indicate that the equilibrium may be forced to the right by employing an auxiliary complexing reagent (X) that binds more strongly to $Pb^{2+}$ than to $Co^{2+}$. In order for the equilibrium

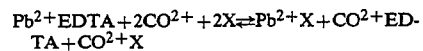

to be shifted to the right, the following conditions must be observed:

(1) $Co^{2+}$ concentration must exceed EDTA concentration by at least 10%

(2) Concentration of $X \geq C_{Co} - C_{EDTA}$ (3) $LogK''_{PbX} \geq 5$ (4) $LogK''_{PbX} - logK''_{CoX} \geq 1$; the difference of 3 log units will cause over 95% conversion of PbEDTA to PbX under these conditions Several compounds fulfill these requirements, including ethylene glycol-bis-($\beta$-aminoethylether)-N,N,N',N'-tetraacetic acid (EGTA), 1-methylethylenediaminetetraacetic acid (MEDTA), meso 2,3-dimercaptosuccinic acid (DMSA), pryocatechol violet, cysteine and penicillamine. While this list is only partial, it will be evident to those skilled in the art that other compounds, not necessarily structurally related, will also be suitable, provided the stated requirements are met.

The percent conversion of lead from the EDTA complex to a complex with one or the other of the listed or other suitable compounds is independent of the lead concentration in the sample. Additionally, the concentrations of $Co^{2+}$, X and EDTA, or the ratios of these substances, do not have to be constant (i.e., from sample to sample) or strictly controlled in order for this approach to be successful, as long as the conditions discussed are fulfilled.

Any agent used for displacing lead from the EDTA complex must not interfere with the function or activity of the enzyme employed for detection. The inventors have tested DMSA, o-phenanthroline, dipyridyl and acetate and found that for isocitrate dehydrogenase the activity, stability and lead inhibition are not adversely affected. Other auxiliary complexing agents may also be useful, including iminodiacetate, citrate and lithium ion. $Li^{+1}$ is known to weaken lead ion binding to bovine serum albumin and is contemplated to be effective in displacing $Pb^{2+}$ from the complex.

In a related approach to effectively displacing lead from the lead/EDTA complex, the inventors have contemplated the use of Co(III) rather than Co(II) to displace $Pb^{2+}$ from the $Pb^{2+}$/EDTA complex. The displacement reaction with Co(III) is thermodynamically favorable.

$$Pb^{2+} + EDTA + Co^{3+} \rightleftharpoons Co^{3+} + EDTA + Pb^{2+}$$
$$(K''_{eq} = 16.3 \text{ at pH } 8.5)$$

The problem is that in neutral pH solutions, Co(III) does not exist in a free form and the ligand exchange reactions involving this ion are kinetically extremely slow. The inventors contemplate treating a sample containing $Pb^{2+}$EDTA with excess $Co^{2+}$ rather than $Co^{3+}$, followed by addition of an oxidizing agent (Ox) which converts $Co^{2+}$EDTA to $Co^{3+}$EDTA. The overall reaction is represented by:

$$Pb^{2+} + EDTA + Co^{2+} + Ox \rightleftharpoons Co^{3+} + Co^{3+}(\text{or } Co^{2+}EDTA) + Pb^{2+} + Red$$

where $R_{ed}$ represents the reduced form of an oxidizing agent, Ox. Excess Ox is then decomposed, employing agents that do not interfere with the enzyme assay. Suitable agents include hydrogen peroxide whose excess can be decomposed by oxidase or catalytically by iron(III). Hypochlorite or ferricyanide may also be employed.

In a practical sense, one need not be limited to EDTA complexes. Without EDTA added to samples, for example, an "auxiliary" complexing agent such as pyrocatechol violet may be added directly to a blood sample and the $Pb^{2+}$ complex measured directly. A freshly drawn blood sample, to prevent coagulation, may be treated with an anticoagulant that binds lead, citrate for example. It is possible that lead complexed with citrate will interact directly with isocitrate dehydrogenase to inhibit catalysis.

Once lead ion is in a form that will inhibit an enzyme sensitive to lead inhibition, i.e., isocitrate dehydrogenase, one preferably detects the inhibition electrochemically employing an enzyme electrode. Electrodes prepared from enzymes sensitive to very low lead levels generate detectable oxidation currents that show a linear decrease in current in the presence of increasing levels of metals to which they are sensitive. The general oxidation/reduction scheme is shown in FIG. 1.

The reactions involved for isocitrate dehydrogenase are shown. A typical mediator is N-methylphenazine methosulfate which operates at 0 V relative to the Ag-/AgCl couple.

ICD isocitrate + NAD+ → α-ketoglutarate + NADH + H+

$NADH + 2\ MED_{ox} \rightarrow NAD+ + 2MED_{red} + H^+$ $2MED_{red} - e^- \rightarrow 2MED_{ox}$ (oxidation current)

Current may be detected directly at the electrode surface during oxidation of the cofactor, either directly or through a mediator.

Pig heart NADP-linked isocitric dehydrogenase (ICD, EC 1.1.1.42), an oxidoreductase, is sensitive to trace levels of lead ion as low as 1 μg/dl. Like many enzymes, ICD is inactive or only slightly active unless $Mg^{++}$ or $Mn^{++}$ is present. In fact, at low concentrations of activator, e.g., <200 ppb $Mn^{++}$, the activity of ICD is proportional to $Mn^{++}$ and may be used to determine activator concentration (Guilbault, 1970). Inactivation by inhibitors is useful for determining inhibitor concentration. Specificity of enzymes for activators, or inhibitors, is not as great as for the natural substrate of the enzyme, but in some cases inhibitor concentration may be selectively determined. Silver and mercury have been determined in the presence of each other using isocitrate dehydrogenase (Mealor and Townshend, 1968). However, until now, there has been no satisfactory rapid amperometric method to determine lead ion based on ICD inhibition, much less a simple method to determine low lead ion concentrations in whole blood.

As used herein, a bioelectrode refers to a single electrode, the working electrode, at the surface of which an electron transfer takes place representing a reaction catalyzed by an enzyme located on or near the surface of the electrode. Such a bioelectrode when set up with an appropriate reference/counter electrode may constitute a biosensor. Within the meaning of the present invention, a biosensor is intended to indicate a system capable of producing a signal that may be related to a reaction catalyzed by an enzyme constituting the biosensor. Biosensors comprising bioelectrodes will operate by producing a current related to the activity of an enzyme catalyzing electron transfer.

Deposition of a lead-detecting enzyme on or near an electrode surface may be accomplished in several ways, including electrodeposition, evaporation, screen printing, spray deposition (e.g., aerosol), or electrolyte deposition. Electrodeposition may be accomplished by setting a working electrode at an appropriate potential, for example 1.6 v vs. a Ag/AgCl reference electrode with a platinum wire counter electrode. Using a two electrode system with a glassy carbon disk electrode held at a fixed position in a cavity in a lucite block, or other suitable material, a platinum plate at the bottom of the cavity serves as a reference/counter electrode. Electrodeposition may be performed at constant current or constant potential and optimized for the enzyme to be deposited.

Solvent evaporation is preferred for ease and convenience. The method is simply performed by applying a fixed amount of enzyme to the electrode surface and then drying at room temperature or near 4° C.

The inventors have developed a highly sensitive method for the determination of lead ion in solution. Isocitrate dehydrogenase, under specific conditions, may be employed in an assay to quantitatively determine lead ion in the range 0–30 μg per deciliter of solution. Assay sensitivity can be adjusted to a desired concentration range for lead by altering one or more of several parameters such as the concentration of isocitric dehydrogenase. Lower enzyme concentrations increase sensitivity to lead ion.

The inventors have found that isocitrate dehydrogenase is affected by the pH of the medium. At pH 7.5, for example, very little if any inhibition is observed at lead concentrations up to about 28 mg per deciliter. Raising the pH to 8 results in about 60% enzyme inhibition in this concentration range. The inhibition at pH 8.5 is about 90%, while raising the pH to 9.0 results in complete inhibition between 0 and 5.5 mg per deciliter lead concentration.

Enzyme sensitivity is also affected by the concentration of $Mn^{+2}$ which is a cofactor for isocitrate dehydrogenase catalyzed reaction. Lower cofactor concentrations to which the enzyme is exposed prior to incubation with the lead increase isocitric dehydrogenase sensitivity. Higher sensitivity to lead ion concentration also results when $Mn^{+2}$ concentration is lower during the incubation process. However, $Mn^{+2}$ concentrations are effective only in a relatively narrow range on the scale of several micromolar so that manipulation of concentration is limited. Temperature also affects the inhibition reaction. Higher temperature increases inhibition, but also increases sensitivity. Temperatures in the range of 18° C. to 37° C. typically increase inhibition rates from 25% to about 85% at the higher temperature.

Generally, therefore, one may select appropriate conditions of solution, pH, enzyme and cofactor concentrations in order to control enzyme sensitivity and selectivity. For convenience, reactions are generally run at room temperature. It must be kept in mind, however, that the factors leading to improved enzyme stability may adversely affect enzyme inhibition and result in a reduction of sensitivity of the assay.

$Mn^{2+}$ is generally employed as cofactor of isocitric dehydrogenase in assay reactions; however, $Mg^{+2}$ is equally effective and can be used in millimolar concentrations as a cofactor, a distinct advantage over $Mn^{2+}$ which is effective only within relatively narrow micromolar concentration ranges. The inventors have discovered that $Mg^{+2}$ is preferable to $Mn^{2+}$ in not binding to other species, a disadvantage frequently encountered with $Mn^{2+}$. Additionally, $Mg^{2+}$ is effective over a relatively broad concentration range without adversely affecting enzyme properties.

The inventors have found that lead ion inhibition of isocitric dehydrogenase may be measured in the presence of some ligands that bind lead ion, including acetate, dipyridyl, o-phenanthroline and the like. However, most blood proteins, such as albumins and strong chelating agents (e.g., EDTA) adversely affect lead ion inhibition of isocitric dehydrogenase depending on the amount of excess of these agents over the lead ion concentration. To solve this problem, the inventors have employed strong chelating reagents to sequester lead ion from interfering blood proteins subsequent to release of the lead from the selected chelating reagent.

Methods

A Pine Instrument dual potentiostat interfaced to an IBM-386 computer was for enzyme electrode measurement. The system is controlled with an ASYST program (J. Zhao, Enzyme Technology Research Group, Inc., 710 West Main Street, Durham, N.C. 27701).

Cyclic voltametry measurements were used to determine amounts of immobilized mediator. Cyclic voltammograms were obtained in the quiescent state. In steady state amperometry experiments the potential was set at 0 V/Ag in stirred buffer with regular sized cell or in quiescent solution with a micro cell and the steady state current was measured. A fixed potential method or chronoamperometric method was used to determine enzyme inhibition.

In the chronometry method, the working electrode was held at a fixed potential while current versus time data were collected with the aid of a computer until steady state was reached. This was observed either from a real-time graphic display and/or the numeric display on the computer screen. After measurement was complete, the computer was set to automatically provide a calibration curve of percentage inhibition vs. inhibitor concentration, heterogeneous binding constants for reversible inhibitors, and/or binding rate constants for irreversible inhibitors. Programs were modified as required.

Enzymes were purchased as indicated and used directly. Results were improved in some cases after the stock enzyme was purified by dialysis. Isocitrate dehydrogenase (Sigma, St. Louis, Mo., ICD Type VI) was dialyzed against buffer containing buffer and manganese ion. If extensive dialysis was performed, substantial enzyme activity was lost; therefore, manganese ion was added to the dialysis buffer.

The following examples are intended to illustrate the practice of the present invention and are not intended to be limiting. Although the invention is demonstrated with isocitrate dehydrogenase to determine lead and alcohol dehydrogenase to determine mercury, numerous variations of these enzymes are contemplated without changing the enzyme's susceptibility to irreversible inhibition by low metal concentrations. Likewise, other enzymes with different substrate specificity but similar selective sensitivity will also be appropriate.

EXAMPLE 1

The following example illustrates determination of trace amounts of lead ion in aqueous medium through the inhibition of isocitrate dehydrogenase (ICDH) in homogeneous solution.

Dialysis of ICDH and Selection of Buffer

Commercially available ICDH (Sigma Chemical Company, St. Louis, Mo.) typically contains considerable amounts of sulfate that interferes with lead ion inhibition of ICDH. Dialysis of ICDH against low ionic strength phosphate buffer caused loss of its activity, which was restored by addition of $Mn^{2+}$. Dialysis against Tris buffer containing a low concentration of $Mn^{2+}$ did not affect ICDH activity.

Buffer selection was important because of potential interactions of the buffer with lead ion. Tris buffer did not cause interference, while carbonate or phosphate buffers were unsatisfactory because of lead ion interactions.

Mediator

NADPH was directly oxidized at high potentials (>0.7 V vs. Ag/AgCl) on carbon electrode. However, at this high potential the background current was high. Additionally, the electrode surface was fouled, presumably due to polymerization during the oxidation process. Direct oxidation of NADPH produced a background current of approximately 900 nA while the total current with isocitrate was only about 1600 nA.

Ferricyanide produced a relatively high background signal because of operation at potentials >0.2 V vs. Ag/AgCl. N-methylphenazine methosulfate produced a background signal of about 20 Na without isocitrate while the total signal with isocitrate was more than 500 nA at 0 V vs. Ag/AgCl.

Microcell

Figure 2:
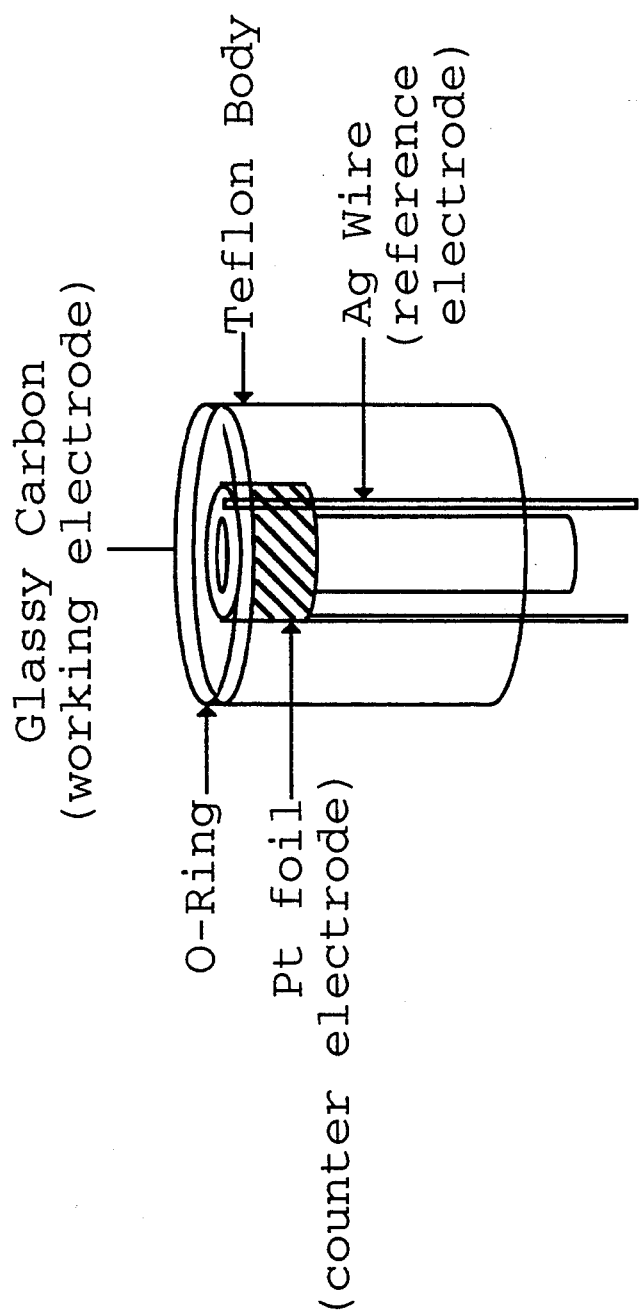
FIG. 2 illustrates a coplanar carbon electrode consisting of a planar three-electrode cell with a sample capacity of about 200 $\mu l$.

A glassy carbon rod of 3 mm diameter was wrapped in teflon tubing as working electrode and surrounded with a layer of Pt foil as the counter electrode with a silver wire placed in between as the reference electrode. At least one layer of teflon was inserted between two of the three electrodes. All three electrode surfaces were on the same plane. Tubing was fixed on the top of the coplanar electrode surface with an O-ring, forming a microcell of 100–200 µl in volume. Microcell configuration is shown in FIG. 2.

Measurement of Lead in Aqueous Solution

To the microcell was added in sequence: 100 µl 50 mM pH 8.5 Tris buffer, ca. 0.3–0.4 units ICDH and, after 15 min, 5 µl 25 mM NMP-MS, 5 µl 60 mM NADP. The background current was measured at 0 V. 10 µl of 0.5M isocitrate was added and the current measured again. The difference in the two signals was taken as due to the oxidation of isocitrate catalyzed by ICDH.

Figure 3:
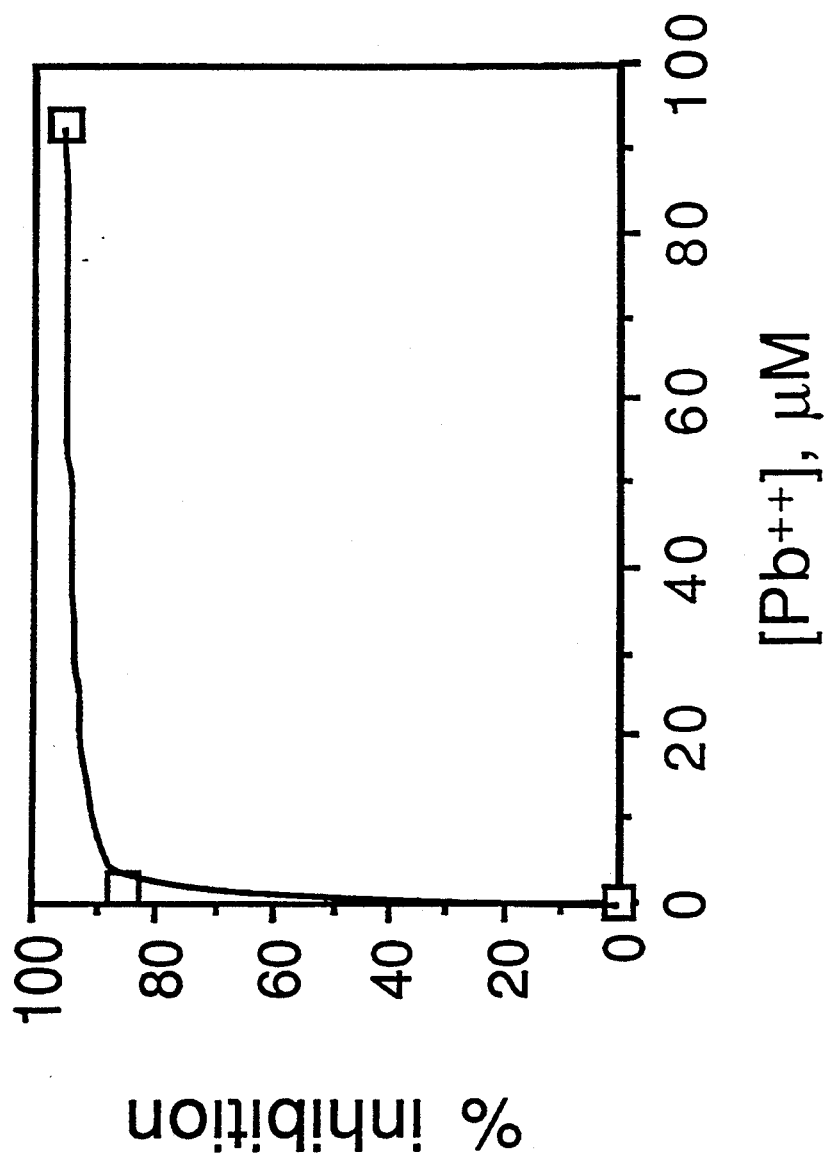
FIG. 3 shows the inhibition of isocitrate dehydrogenase by lead in various buffer solutions.

To measure lead inhibition of ICDH, lead ion was added to the above solution after addition of ICDH but 15 min prior to the addition of NMP-MS and NADP. The current difference with isocitrate was due to inhibition of ICDH by the added lead. Typical data are shown in Table 1. FIG. 3 indicates the sensitivity of the electrode to lead ion concentrations in the submicromolar range.

TABLE 1

| $[Pb^{++}]/\mu M$ | 0 | 1.89 | 90.9 |
|---|---|---|---|
| current/nA | 1480 | 218 | 26 |
| % inhibition | 0 | 85.3 | 98.2 |

$K_i$ = 0.33 µM or 6.83 µg/dl lead

The presence of the mediator NMP-MS interfered with inhibition of the enzyme by added lead ion.

EXAMPLE 2

The following example illustrates a typical preparation of an active enzyme adsorbed to colloidal gold. Such enzymes may be used to prepare bioelectrodes, generally by evaporative or electrodeposition of the enzyme/colloidal gold solution onto a suitable electrode surface.

Colloidal Gold Adsorbed ICDH

Colloidal gold solutions were prepared by adding a solution of 1% aqueous sodium citrate to a boiling rapidly stirred solution of gold trichloride and refluxing for 30 min. Final concentrations (w/w) were 0.01% $HAuCl_4$ and 0.03% sodium citrate. The particle size was estimated by filtration of the sol through polycarbonate membranes (Nuclepore Corporation, Pleasanton, Calif.) of varying pore size using an Amicon micro ultrafiltration unit. Approximately 40% of the sol passed through a 500 A Nuclepore filter and was quantitatively collected on a 300 A Nuclepore filter.

The gold sol was concentrated by centrifugation at room temperature. The concentrated sol was mixed with appropriate amounts of dialyzed isocitrate dehydrogenase solutions. Then a fixed amount of the Au-ICDH sol was evaporated on a coplanar carbon electrode surface and the activity measured. The ICDH concentration profile in the Au-ICDH sol was constructed vs. the measured immobilized activity to determine the optimum composition of the Au-ICDH sol.

At low ICDH loadings, the enzyme activity was too low to generate a detectable signal. As the loading increased the ICDH-Au sol became unstable and precipitated. At higher loadings the sol became stable and the immobilized ICDH activity was good.

Electrochemical Measurement of Immobilized ICDH Activity

After evaporation of ICDH-Au sol onto a carbon electrode surface, the electrode surface exhibited a yellow-gold appearance which was not washed off. The electrode surface was briefly rinsed with water to remove any loosely bound material before measurements were made. Buffer solution with NMP-MS and NADP was added to the microcell. Background current was measured, then isocitrate added and current again measured. Typical background and sample signals were 25 and 550 nA respectively.

The basic operational principle for ICDH is shown in FIG. 2. An electron transfer mediator for efficient charge coupling with the electrode surface is required. When substrate concentration is sufficiently high, the generated oxidation current signals are directly proportional to the total amount of enzyme immobilized on the electrode surface. A mediator carries electrons between the enzyme(cofactor) and the electrode surface. Substrate is consumed with the production of a catalytic current.

EXAMPLE 3

The following example illustrates several methods contemplated for the detection of lead in whole blood using the bioelectrode of Example 2. The addition of whole blood to the microcell of Example 2, regardless of lead content, reduced current signal.

A bare coplanar carbon electrode was used to determine whether a current could be generated. In a microcell containing 0.1 ml Tris buffer with appropriate amounts of ICDH, NMP-MS, NADP and isocitrate (see Example 1) the electrode produced an oxidation current at 0 V relative to Ag/AgCl.

Whole blood interfered with the electrode response to lead in a solution where ICDH, NADP, NMP-MS, isocitrate, blood and buffer are mixed together. Presence of the blood increased the viscosity of the mixture and slowed the diffusion process of molecules such as NADP (mw ca. 743) and NMP-MS which are fairly large and have only limited concentrations in practical usage. Several methods are envisioned to overcome this problem, including:

Co-immobilization of Key Elements

The interference arises from the low usable concentrations of ICD, NADP and NMP-MS. When diffusion processes are slow because of solution viscosity, the generated electric signal is reduced. If all key elements required for signal generation are immobilized on or near the electrode surface, long range diffusion or mass transfer is no longer necessary for signal generation and interference is eliminated.

Alternatively, a mediator in the form of an insoluble conducting salt NMP-TCNQ, NADP and ICD are co-immobilized at the electrode surface. Only enzyme substrate, isocitrate, is then required for signal generation and this is added in excess to overcome diffusion limitation.

Co-immobilization of ICD, NADP and an insoluble mediator is feasible and practical. It is contemplated that blood interference will be greatly reduced or eliminated.

Two-Step Method

Lead inhibition and signal measurement will be separately performed. The bioelectrode is first treated with a blood sample containing lead for a fixed amount of time during which lead ion will inactivate the enzyme. The blood is rinsed off and signal measurement quickly determined. Rinsing will remove the blood and reduce blood interference without altering lead ion inhibition. The two-step method will eliminate any blood interference and will remove any potentially interfering species in the blood sample that are electrochemically active.

Alternatively, the blood sample is treated before measurement. Several appropriate methods of treatment are contemplated.

Dilution of Sample

The blood sample will be diluted with a buffer containing a detergent such as SDS to hemolyze the blood, or, treated with a lead complexing agent. Appropriate dilution of the sample will reduce blood interference to a tolerable level and may facilitate the inhibition process.

Solvent Extraction

Lead in blood will be extracted into an organic solvent, in a manner analogous to that routinely used in the atomic absorption method of lead determination. Once extracted into an organic phase, inhibition is performed directly in the organic solvent, provided that the solvent selected is one in which the immobilized enzyme is stable. Alternatively, the enzyme electrode is treated so that there is a stationary aqueous layer on the electrode surface allowing lead to partition from the organic phase to the thin aqueous layer where it will inhibit the immobilized enzyme. The electrode surface is coated with a thin hydrogel layer above the immobilized enzyme, the gel being wetted prior to application of the organic solvent into which the lead ion has been extracted.

Yet another option is to extract the organic phase containing the lead into the aqueous phase prior to inhibition measurements.

Lead-ion Selective Membrane

Lead selective ionophore-doped PVC membranes have been studied by others and shown to operate in the submicromolar range (Kamata and Onoyama, 1991). The combination of the disclosed bioelectrode and a lead-sensitive membrane will increase total selectivity and sensitivity.

EXAMPLE 4

This example illustrates the co-immobilization of ICDH and a mediator on the electrode surface.

A glassy carbon electrode was first coated with NMP-TCNQ-PVC paste and dried. Then ICDH-Au sol was evaporated onto the coating surface. Then Tris buffer with NADP was added and background current of 5 nA measured at 0 V. The signal increased to 231 nA on addition of isocitrate. This indicated that both ICDH and mediator could be immobilized on the electrode surface.

EXAMPLE 5

This example illustrates co-immobilization of ICDH, mediator and cofactor on an electrode surface. Immobilization is shown with colloidal gold; however, other forms of immobilized enzyme are contemplated, including membrane immobilization or surface deposition.

NADP was added to the NMP-TCNQ-PVC paste before coating onto a glassy carbon electrode surface. ICDH-Au sol was then evaporated onto the coating. The formed electrode contained the key elements for signal generation, except the substrate, isocitrate.

EXAMPLE 6

The following example illustrates a bioelectrode sensitive to low levels of mercury ion.

Detection of Mercury Ion in Aqueous Solution

Figure 4:
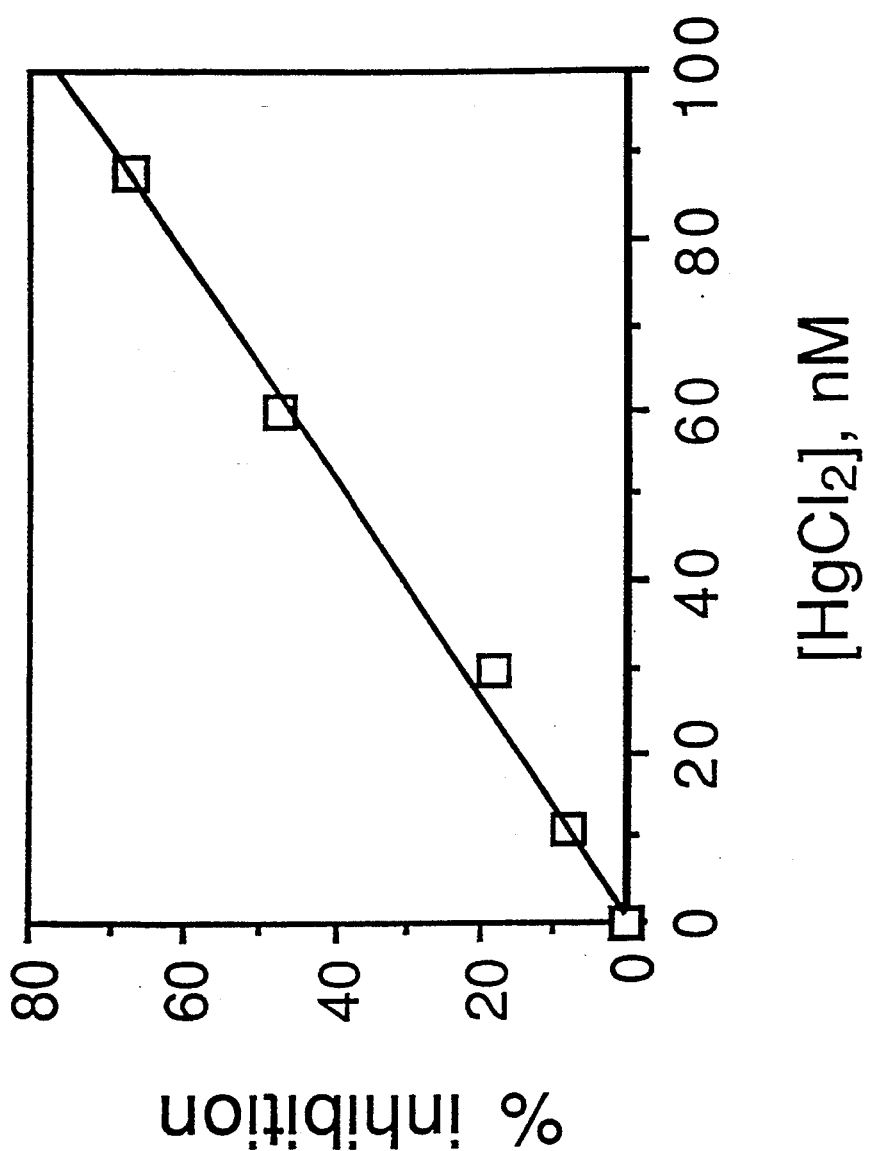
FIG. 4 illustrates the linear amperometric response to mercury ion using a colloidal gold/ADH bioelectrode prepared by deposition on glassy carbon.

A bioelectrode was prepared from colloidal gold adsorbed alcohol dehydrogenase according the procedure of Example 2 for ICD. Measurements were made in the microcell as described in Example 1 using various concentrations of mercury. The linear portion of the curve is shown in FIG. 4, indicating a linear response in at nanomolar levels of mercury ion. The inhibition was irreversible and was specific for mercury in the presence of added lead ion.

EXAMPLE 7

The inventors have shown that less than 1 $\mu$g/dL of lead in solution may be measured employing the enzyme isocitrate dehydrogenase. The measurements are sensitive to several factors, including pH, enzyme concentration, co-factor concentration and temperature. The following example illustrates the effect of pH on enzyme inhibition.

Inhibition of Isocitrate Dehydrogenase by Lead ion solution

Inhibition of the enzyme isocitrate dehydrogenase was calculated based on the amperometric signal (I) which is the mediator oxidation current measured with a glassy carbon electrode at an applied potential of +100 mV. Inhibition was determined as $(I_{uninhibited} - I_{inhibited})/I_{uninhibited}$. 50 mM Tris buffer at various pH values as shown in Table 2 was used with 1.0 U/mL enzyme in the solution.

As shown in Table 2, greatest sensitivity was obtained at pH 9.0 at which the enzyme was completely inhibited at lead ion concentrations of 5.5 $\mu$g/dL. Significant inhibition, approximately 87%, was observed at pH 8.5 by concentrations of lead at 27.6 $\mu$g/dL while there was no significant inhibition at 27.6 µg/dL lead at pH 7.5.

TABLE 2
INHIBITION OF ISOCITRATE DEHYDROGENASE[1] BY LEAD ION

| $Pb^{+2}$ µg/dL | pH 7.5 | | pH 8.0 | | pH 8.5 | | pH 9.0 | |
|---|---|---|---|---|---|---|---|---|
| | Current (nA) | Lead Inhibition (%) | Current (nA) | Lead Inhibition (%) | Current (nA) | Lead Inhibition (%) | Current (nA) | Lead Inhibition (%) |
| 0 | 751 | 0 | 713 | 0 | 776 | 0 | 832 | 0 |
| 5.5 | 749 | 0 | 673 | 6 | 636 | 18 | 4 | 99 |
| 11.1 | 754 | 0 | 613 | 14 | 522 | 33 | 21 | 98 |
| 16.6 | 760 | −1 | 532 | 25 | 406 | 48 | | |
| 22.1 | 750 | 0 | 439 | 38 | 241 | 69 | | |
| 27.6 | 761 | −1 | 303 | 58 | 99 | 87 | | |

[1] 1.0 U/mL in 50 mM tris buffer

EXAMPLE 8

A major problem in the measurement of lead in blood is the interference by various blood proteins and, as in the majority of clinical samples, the presence of excess amounts of EDTA. The inventors have discovered that lead chelated with EDTA is exchangeable with cobalt-(II). As shown in this example, lead Pb(II) is displaced from EDTA by cobalt(II) and detected by its inhibition of isocitrate dehydrogenase (ICDH).

Computer simulations were developed to assess lead binding to blood components. These calculations showed that Co(II) displaced lead complexed with EDTA under conditions of the blood lead assay.

Micromolar concentrations of lead were determined through ICDH inhibition in the presence of 1 mM $CoSO_4$. Inhibition of the enzyme at several lead concentrations is shown in Table 3.

TABLE 3

| Lead Ion Concentration (µM) | Inhibition (%) |
|---|---|
| 0 | 0 |
| 2.4 | 24 |
| 4.8 | 46 |
| 12 | 71 |

[1] $CoSO_4$ concentration was 1 mM

Micromolor concentrations of lead were detected by ICDH inhibition in the presence of 2 mM EDTA and 2.5 mM $CoSO_4$. In the absence of $CoSO_4$, no inhibition was observed. Inhibition at several lead ion concentrations is shown in Table 4.

TABLE 4

| Lead Ion Concentration (µM) | Inhibition(%) |
|---|---|
| 0 | 0 |
| 12 | 23 |
| 36 | 32 |
| 121 | 47 |

[1] Concentration of EDTA was 2 mM; concentration of $CoSO_4$ was 2.5 mM

EXAMPLE 9

The activity of isocitrate dehydrogenase and its response is affected by several factors. The following data indicate effect of heating on activity and rates.

Heating

Figure 5:
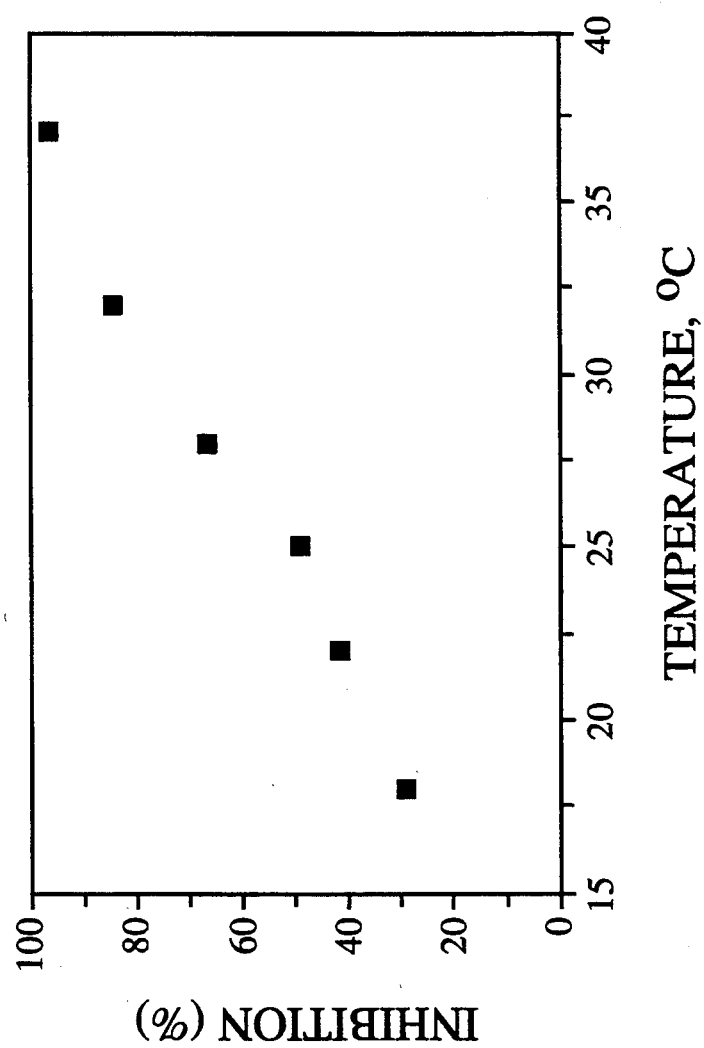
FIG. 5 shows the effect of temperature on inhibition of isocitrate dehydrogenase.

A solution of isocitrate dehydrogenase (10 nM) was incubated for 15 min at various temperatures between 18° C. and 37° C. and rate of lead inhibition measured. Inhibition rates increased approximately linearly from about 25% to 85% at a lead concentration of 4 µM (FIG. 5).

pH

Figure 6:
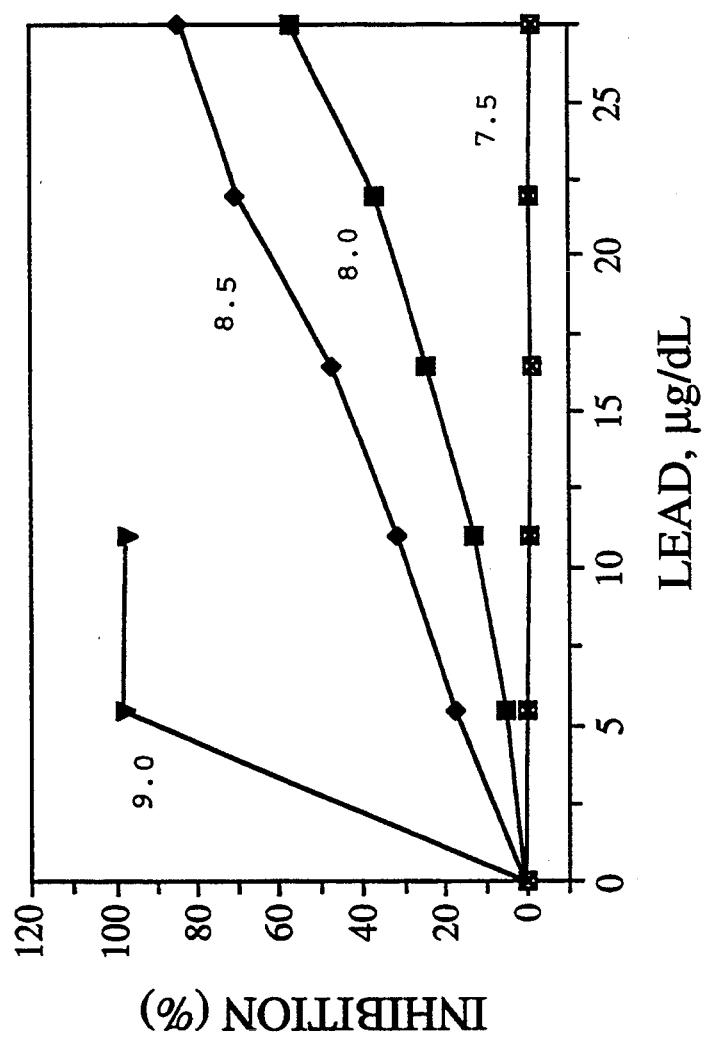
FIG. 6 shows the effect of pH on inhibition of ICDH at various lead ion concentrations; ▼ at pH 9.0; ◆ at pH 8.5; ■ at pH 8.0; and ✗ at pH 7.5.

The effect of pH and lead ion concentration on inhibition of ICDH is shown in FIG. 6.

EXAMPLE 10

Several compounds were tested in combination with $Co^{2+}$ for ability to displace Pb(II) from $Pb^{2+}$+EDTA complexes, employing computer simulations.

$$Pb^{2+}+EDTA+Co^{2+} = Co^{2+}+EDTA+PbX$$

Selection was based on thermodynamic considerations of stability constants to assure that equilibrium would lie to the right, that is, the compound would bind more tightly to Pb(II) than binding to Co(II).

Conversion of PbEDTA to PbX

The compounds shown in Table 5 were set up in a computer simulation as added to a buffered solution containing 1 µM $Pb^{2+}$, 4 mM EDTA, 5 mM $Co^{2+}$ and the selected compound at 1 mM. Displacement of $Pb^{2+}$ ranged from 38% for dimercaptosuccinic acid to virtually complete for cysteine.

TABLE 5

| X | log"$K_{PbX}$ | logK"$_{CoX}$ | Percent Pb released |
|---|---|---|---|
| EGTA | 12.07 | 10.86 | 58 |
| MEDTA | 13.66 | 11.85 | 85 |
| DMSA | 12.48 | 10.48 | 38 |
| Pyrocatechol violet | 6.75 | 3.60 | 94 |
| Cysteine | 9.14 | 5.93 | 99 |
| Penicillamine | 8.95 | 6.72 | 94 |

REFERENCES

The references listed below are incorporated herein by reference to the extent that they supplement, explain, provide a background for or teach methodology, techniques and/or compositions employed herein.

Albery, W. J., Cass, A. E. G., Mangold, B. P. and Shu, Z. X. Biosensors & Bioelectronics 5, 397 (1990).

Almestrand L., Betti, M., Hua, C., Jagner, D. and Renman, L., Anal. Chim. Acta 209, 339–343 (1988).

Baum, P. and Czok, R., Biochem. Z. 332, 121 (1959).

Botre, C., Botre, F., Jommi, G. and Signorini, R., J. Med. Chem. 29, 1814 (1986).

Chemical and Engineering News, page 17, Oct. 14, 1991.

Fair, B. D. and Jamieson, A. M., J. Colloid Interface Sci. 77, 525 (1980).

Guilbault, G. G., Brignac, P., Jr., and Zimmer, M., Anal. Chem. 40, 190–196 (1968).

Guilbault, G. G., "Enzymatic Methods of Aalysis", Pergamon Press, 1970.

Holleck, G. L., J. Electrochem. Soc. 119, 1158 (1972).

Kamata, S. and Onoyama, K., Anal. Chem. 63, 1295 (1991).

Kratochvil, B., Boyer, S. L., and Hicks, G. P., Anal. Chem. 39, 45–51 (1967).

Linde, H. W., Anal. Chem. 2092 (1959).

Mealor, D., and Townshend, A., Talanta 15, 747 (1968).

Morrissey, B. W. and Han, C. C., J. Colloid Interface Sci. 65, 423 (1976).

Sheikh, R. A. and Townshend, A., Talanta 21, 401–409 (1974).

Smit, M. H. and Cass, A. E. G., *Anal. Chem.* 62, 2429–2436 (1990).

Toren, E. C. and Burger, F. J., *Mikrochimica Acta (Wien)*, 538–545 (1968).

Tran-Minh, C. Pandey, P. C. and Kumaran, S., *Biosensors & Bioelectronics* 5, 461 (1990).

What is claimed is:

1. A method of determining lead levels in blood, comprising:

admixing a blood sample with an agent specifically binding lead to form a lead complex;

displacing the lead with a metal ion to form an irreversible metal ion complex; and detecting the displaced lead and determining the lead levels in blood by electrochemical measurement.

2. The method of claim 1 wherein the irreversible metal ion complex is formed by oxidizing the metal ion.

3. The method of claim 2 wherein the metal ion is oxidized from a plus two to a plus three oxidation state.

4. The method of claims 1 or 2 wherein the electrochemical determination is with a bioelectrode which consists essentially of an immobilized enzyme in contact with a conducting surface and wherein inhibition of the enzyme by lead ions detectably affects current generated from redox reactions catalyzed by the enzyme when the bioelectrode is coupled with a reference electrode.

5. The method of claim 4 wherein the enzyme is isocitrate dehydrogenase.

6. The method of claim 1 wherein the agent specifically binding lead is dimercaptosuccinic acid, ethylenediaminetetraacetic acid, methylethylenediaminetetraacetic acid, or ethylene glycol-bis-($\beta$-aminoethylether) N,N,N',N'-tetraacetic acid.

7. The method of claim 1 wherein the agent specifically binding lead is ethylenediamine tetraacetic acid.

8. The method of claim 1 wherein the displacing metal ion is cobalt(II) or iron(II).

9. The method of claim 1 wherein the displacing metal ion is in a plus two oxidation state.

10. The method of claim 1 wherein the displacing metal is cobalt (II).

11. The method of claim 10 wherein cobalt(II) is oxidized to cobalt(III).

* * * * *